United States Patent
Feigl

(10) Patent No.: US 10,792,033 B2
(45) Date of Patent: Oct. 6, 2020

(54) DEVICES AND METHODS FOR POSITIONING SUTURES

(71) Applicant: A&P Feigl Family Limited Partnership, McAllen, TX (US)

(72) Inventor: Alexander J. Feigl, McAllen, TX (US)

(73) Assignee: A&P FEIGL FAMILY LIMITED PARTNERSHIP, McAllen, TX (US)

( * ) Notice: Subject to any disclaimer, the term of this patent is extended or adjusted under 35 U.S.C. 154(b) by 105 days.

(21) Appl. No.: 15/799,640

(22) Filed: Oct. 31, 2017

(65) Prior Publication Data

US 2018/0271517 A1    Sep. 27, 2018

Related U.S. Application Data

(60) Continuation of application No. 12/177,694, filed on Jul. 22, 2008, now Pat. No. 9,801,623, which is a division of application No. 10/077,618, filed on Feb. 15, 2002, now Pat. No. 7,402,166.

(51) Int. Cl.
   *A61B 17/04* (2006.01)
   *A61B 17/06* (2006.01)
   *A61B 17/29* (2006.01)

(52) U.S. Cl.
   CPC .......... *A61B 17/0482* (2013.01); *A61B 17/06* (2013.01); *A61B 2017/2947* (2013.01)

(58) Field of Classification Search
   CPC .. A61B 17/0482; A61B 17/0469; A61B 17/06
   See application file for complete search history.

(56) References Cited

U.S. PATENT DOCUMENTS

| | | | | |
|---|---|---|---|---|
| 3,470,875 A | * | 10/1969 | Johnson | A61B 17/064 606/145 |
| 4,164,225 A | * | 8/1979 | Johnson | A61B 17/04 227/19 |
| 5,391,174 A | * | 2/1995 | Weston | A61B 17/0469 606/148 |
| 5,527,322 A | * | 6/1996 | Klein | A61B 17/0057 606/144 |
| 5,810,849 A | * | 9/1998 | Kontos | A61B 17/0057 606/144 |
| 5,972,005 A | * | 10/1999 | Stalker | A61B 17/0057 606/144 |
| 6,136,010 A | * | 10/2000 | Modesitt | A61B 17/0057 606/139 |

(Continued)

*Primary Examiner* — Alexander J Orkin
(74) *Attorney, Agent, or Firm* — Norton Rose Fulbright US LLP

(57) ABSTRACT

A device that facilitates the placement of one or more needles and their attached sutures in the body of a surgical patient is disclosed. The device contains one or more needle guide channels in which one or more needles may be backloaded. The device also contains one or more lumens extending though the body of the device. One or more sutures may be coupled to the one or more needles, and threaded through the lumen. The one or more needles may then be advanced out of their respective needle guide channels by pulling on one end of one or more sutures. When one end of a suture is pulled, the attached needle is advanced out of the device and will pierce and be positioned in the tissue that is located adjacent to the device.

14 Claims, 10 Drawing Sheets

(56) References Cited

U.S. PATENT DOCUMENTS

| | | | |
|---|---|---|---|
| 6,231,561 B1* | 5/2001 | Frazier | A61B 17/0401 604/500 |
| 6,767,352 B2* | 7/2004 | Field | A61B 17/0469 606/148 |

* cited by examiner

DEVICES AND METHODS FOR POSITIONING SUTURES

CROSS-REFERENCE TO RELATED APPLICATIONS

This is a continuation of application Ser. No. 12/177,694, filed Jul. 22, 2008, now U.S. Pat. No. 9,801,623, which is a divisional of U.S. Ser. No. 10/077,618, filed Feb. 15, 2002, now U.S. Pat. No. 7,402,166, which are both incorporated by reference without disclaimer.

BACKGROUND OF THE INVENTION

1. Field of the Invention

The present invention relates generally to the field of medical devices. More particularly, it relates to an instrument used in the field of suture placement during surgery. Even more particularly, it relates to an instrument that may be used to position one or more needles in locations that are difficult to suture using conventional methods.

2. Description of Related Art

In the field of medical surgery, suture placement is an integral part of the vast majority of operations. Many surgical procedures entail the placement of a difficult stitch or stitches. Traditional needle advancement and positioning instruments almost exclusively use a hemostat-like tool that allows a needle to be gripped by the tool and then advanced into the tissue being sutured. For instance, in either open or traditional laparoscopic suturing procedures, a needle is often grasped by one of these traditional instruments, and the needle, along with the suture coupled to the needle, is placed in the desired position and driven through tissue. The needle is then exchanged or adjusted with a second instrument.

Such tools are disadvantageous because it is often difficult for a doctor to grasp and position the needle. Additionally, many of these devices only allow for the placement of a single needle at a time. Furthermore, using traditional devices to position multiple needles in the tissue of a patient is also time consuming, and is therefore detrimental to the patient as the length of the surgical procedure is increased. A need therefore exists for an instrument that would allow for the precise and rapid positioning of needles during surgical procedures.

SUMMARY OF THE INVENTION

The present invention is directed to a medical device for positioning sutures in the body of a surgical patient. In one embodiment, the device comprises a body, a lumen, and a first needle guide channel. A "lumen" is simply a passageway. The body of the device may have a variety of shapes that are advantageous for the placement of the device within the body of the patient. In one embodiment, the body may be tapered at one end.

The lumen is formed in the body, and extends from a first lumen opening formed in the body to a second lumen opening formed in the body. The lumen is of sufficient diameter to receive a length of suture.

The first needle guide channel is also formed in the body, and may extend from a first needle guide channel opening formed in the body to a second needle guide channel opening formed in the body. In another embodiment, the needle guide channel may extend from only a first needle guide channel opening formed in the body. The needle guide channel may have a variety of shapes. For example, in one embodiment, the needle guide channel is arcuate shaped. As used herein, an "arcuate" shaped needle guide channel need not be a perfect arch. Instead, such a needle guide channel is curved, and may or may not have a break in the curve, provided a curved needle can still move within the needle guide channel. The lumen and first needle guide channel are configured in operative relation with each other such that a needle is backloaded into the first needle guide channel will be advanced out of the first needle guide channel by pulling on a length of suture that is connected to the needle and threaded through the lumen.

The medical device may also comprise a handle coupled to the body. The handle may be coupled to the body by a connector piece. The connector piece may be bendable such that it can be fixed in a variety of positions.

In another embodiment, the device may comprise a plurality of needle guide channels. Each of the one or more needle guide channels may extend from its own first needle guide channel opening formed in the body to its own second needle guide channel opening formed in the body. In another embodiment, each of the one or more needle guide channels will extend from only its own first needle guide channel opening formed in the body. Each of the one or more additional needle guide channels may be configured in operative relation with the lumen such that a needle backloaded into any of the one or more additional needle guide channels will be advanced out of the additional needle guide channel by pulling on a length of suture that is connected to the needle and threaded though the lumen.

The plurality of needle guide channels may come in a variety of shapes. In one embodiment, one or more of the one or more additional needle guide channels is arcuate shaped. Additionally, each of the one or more additional needle guide channels and the first needle guide channel may be arcuate shaped. The plurality of needle guide channels may also be positioned in a variety of ways. In one embodiment, the needle guide channels are circumferentially positioned around the body. In another embodiment, the needle guide channels are circumferentially positioned around the body and are equidistant from each other.

In another embodiment, the invention is directed to a medical device comprising a body, a lumen, and a first needle guide channel. The lumen extends from a first lumen opening formed in the body to a second lumen opening formed in the body and is adapted to receive a length of suture. A first arcuate shaped needle guide channel extends from a first needle guide channel opening formed in the body to a second needle guide channel opening formed in the body. The device may also comprise a handle coupled to the body. The handle may be coupled to the body by a connector piece. The device may also comprise one or more additional needle guide channels. Each of the one or more additional needle guide channels may extend from its own first needle guide channel opening formed in the body to its own second needle guide channel opening formed in the body. Each of the one or more additional needle guide channels may have an arcuate shape. The first needle guide channel and each of the one or more additional needle guide channels may be circumferentially positioned around the body and may be equidistant from each other.

In yet another embodiment, the device may be comprised of a body, a lumen, a first needle guide channel, a first needle, and a length of suture attachable to the first needle. A length of suture that is "attachable" to a needle means that the suture is not necessarily attached to the needle, but can be attached to the needle. The body may be a variety of shapes, and may be tapered. The lumen may extend from a first lumen opening formed in the body to a second lumen opening formed in the body and is adapted to receive a length of suture. The first needle guide channel may extend from a first needle guide channel opening formed in the body to a second needle guide channel opening formed in the body. The first needle is adapted to be at least partially contained in the first needle guide channel. The length of suture may be coupled to the first needle. The lumen and first needle guide channel are configured in operative relation with each other such that when the needle is backloaded into the first needle guide channel, the needle will be advanced out of the first needle guide channel by pulling on the length of suture that has been connected to the needle and threaded through the lumen. The first needle guide channel may also be arcuate shaped.

The medical device may comprise a handle coupled to the body. The handle may be coupled to the body by a connector piece. The connector piece may be bendable such that it can be fixed in a variety of positions. Furthermore, the device may comprise one or more additional needle guide channels, one or more additional needles, and one or more additional lengths of suture. Each of the one or more needle guide channels may extend from its own first needle guide channel opening formed in the body to its own second needle guide channel opening formed in the body. Each of the one or more additional needle guide channels may have its own additional needle adapted to be at least partially contained in the additional needle guide channel. Each additional needle may have its own additional length of suture. Each additional length of suture may be attached to its own additional needle. Each of the one or more additional needle guide channels may be configured in operative relation with the lumen such that when the additional needle corresponding to the additional needle guide channel is backloaded into the additional needle guide channel, the additional needle will be advanced out of the additional needle guide channel by pulling on the additional length of suture that is connected to the additional needle and threaded though the lumen. One or more of the additional needle guide channels may be arcuate shaped. The first needle guide channel and each of the one or more additional needle guide channels may be circumferentially positioned around the body, and in addition may be equidistant from each other.

In another embodiment, the device may comprise a body, a lumen, and a first needle guide channel. The body may be a variety of shapes, and in particular may be tapered. The lumen may extend from a first lumen opening formed in the body to a second lumen opening formed in the body and is adapted to receive a length of suture. The first needle guide channel extends from a first needle guide channel opening formed in the body, and the needle guide channel may be arcuate shaped. The lumen and first needle guide channel are configured in operative relation with each other such that when a length of suture is threaded through the lumen and is connected to a needle that is backloaded into the first needle guide channel, and the length of suture is pulled in a first direction, the needle is advanced out of the needle guide channel in a second direction. The first direction has a positive longitudinal component and the second direction has a negative longitudinal component.

The device may also comprise a handle coupled to the body. The handle may be coupled to the body by a connector piece that may be bendable such that it can be fixed in a variety of positions.

The device may also comprise one or more additional needle guide channels. Each of the one or more needle guide channels may extend from its own first needle guide channel opening formed in the body. The lumen and each of the one or more additional needle guide channels are configured in operative relation with each other such that when a length of suture is threaded through the lumen and is connected to a needle that is backloaded into one of the one or more additional needle guide channels, and the length of suture is pulled in a first direction, the needle is advanced out of the needle guide channel in a second direction. The first direction has a positive longitudinal component and the second direction has a negative longitudinal component. Each of the one or more additional needle guide channels may be arcuate shaped. The first needle guide channel and each of the one or more additional needle guide channels may be circumferentially positioned around the body, and additionally may be equidistant from each other.

In a further embodiment, the device is comprised of a first member and a second member. The first member has a first handle and a first jaw. The second member has a second handle and a second jaw. The second member is pivotally connected to the first member. The first jaw comprises of a lumen and a first needle guide channel. A first lumen may extend from a first lumen opening formed in the first jaw to a second lumen opening formed in the first jaw. The lumen should be adapted to receive a length of suture. The first needle guide channel extends from a first needle guide channel opening formed in the first jaw, and the needle guide channel may be arcuate shaped. The lumen and first needle guide channel are configured in operative relation with each other such that a needle that is backloaded into the first needle guide channel will be advanced out of the first needle guide channel by pulling on a length of suture that is connected to the needle and threaded through the lumen.

The device may further comprise one or more additional needle guide channels, which may also be arcuate shaped. Each needle guide channel may extend from its own first needle guide channel opening formed in the first jaw. Each of the one or more additional needle guide channels may be configured in operative relation with the lumen such that a needle that is backloaded into any of the one or more additional needle guide channels will be advanced out of the additional needle guide channels by pulling on a length of suture that is connected to the needle and threaded though the lumen. Two needle guide channels in the first jaw may cross each other.

In a further embodiment, the second jaw may comprise a lumen and a first needle guide channel. The second jaw may be configured in the same manner previously discussed with respect to the first jaw.

In yet another embodiment, the invention is a method of needle placement. The method comprises attaching a first length of suture to a first needle. The first needle is then positioned in the desired location. The first length of suture is then advanced in a first direction, thereby causing the needle to move in a second direction. The first direction has a positive longitudinal component and the second direction has a negative longitudinal component.

The method may further comprise attaching one or more additional length of sutures to one or more additional needles. The needles may then be positioned at a desired location. The one or more additional sutures may be advanced in a first additional direction, thereby causing the one or more additional needles attached to the advancing one or more additional lengths of sutures to move in a second additional direction. The first additional direction will have a positive longitudinal component and the second additional direction will have a negative longitudinal component.

In further embodiments, the method comprises using a device according to any of the embodiments of the present invention to position the one or more needles.

Other embodiments of the present medical devices and methods will be apparent from the detailed description below.

BRIEF DESCRIPTION OF THE DRAWINGS

The following drawings form part of the present specification and are included to further demonstrate certain aspects of the present invention. The invention may be better understood by reference to one or more of these drawings in combination with the description of illustrative embodiments presented herein. The devices shown in the drawings are not necessarily drawn to scale.

FIG. 2A shows a generally straight needle guide channel extending from a single opening. FIG. 2B shows an arcuate needle guide channel that also extends from a single opening.

FIG. 4A shows a lumen that extends from a first opening formed in the side of the body to a second opening formed at one end of the body. FIG. 4B shows a lumen that extends from a first opening formed in the needle guide channel to a second opening formed in one end of the body. FIG. 4C shows a device having multiple lumens.

DESCRIPTION OF ILLUSTRATIVE EMBODIMENTS

As a preliminary matter, it should be noted that in this document (including the claims), the terms "comprise" (and any form thereof, such as "comprises" and "comprising"), "have" (and any form thereof, such as "has" and "having"), and "include" (and any form thereof, such as "includes" and "including") are open-ended transitional terms. Thus, a thing (such as a medical device or a needle placement method) that "comprises," "has," or "includes" one or more elements possesses those one or more elements, but is not limited to only possessing those one or more elements. For example, a medical device "comprising" a body, a lumen extending between openings formed in the body, and a first needle guide channel extending between needle guide channel openings formed in the body is a medical device that has, but is not limited to only having, these items. In other words, the medical device possesses a body, a lumen extending between openings formed in the body, and a first needle guide channel extending between needle guide channel openings formed in the body, but is not excluded from possessing additional elements or features that are not listed.

The device of the present invention facilitates the placement of one or more needles and their attached sutures in areas of the body of a surgical patient that may otherwise be difficult to suture. The device allows for the quick and accurate placement of one or more needles in difficult stitches with one motion. The device may be positioned at various places within the body of a surgical patient. Once the device is positioned, a needle that has been loaded into the device may be positioned in the tissue surrounding the device by pulling on a suture coupled to the needle. When the suture is pulled, the needle is advanced out of the device and will pierce and be positioned in the tissue that is located adjacent to the device.

Figure 1:
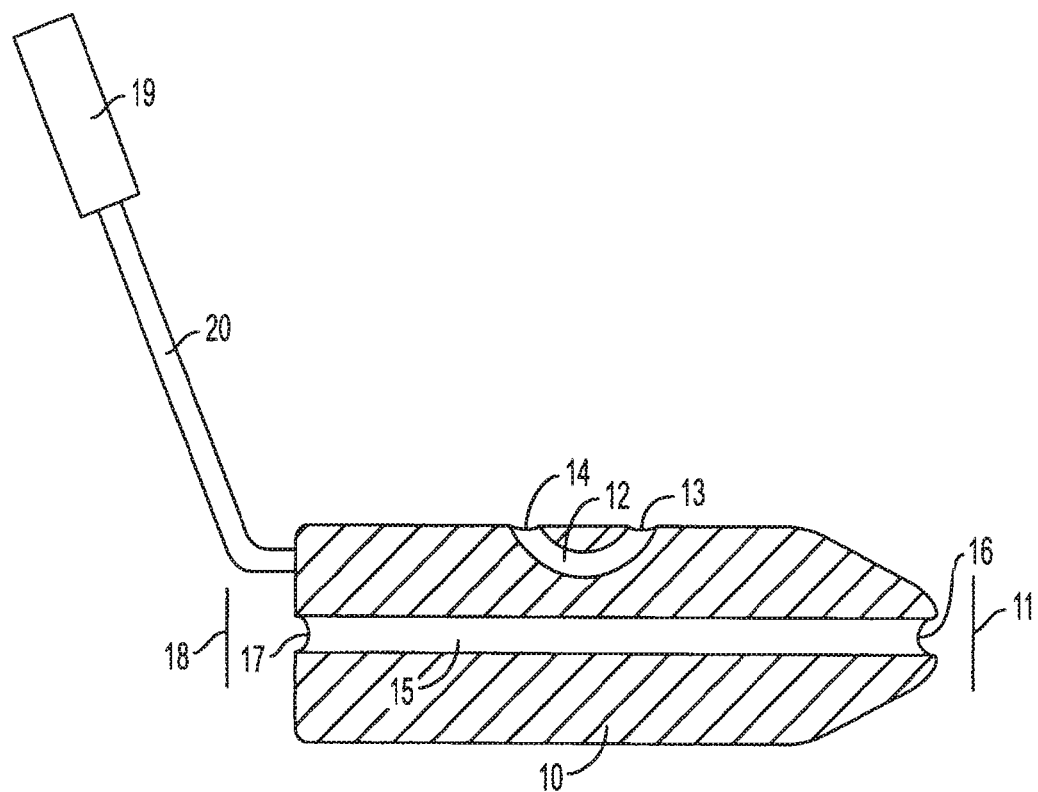
FIG. 1 shows one embodiment of the present invention, wherein the body of the device is depicted in cross section and comprises one arcuate shaped needle guide channel that extends from a first needle guide channel opening to a second needle guide channel opening.

FIG. 1 shows one embodiment of a device of the present invention. The device has a body 10 that may be made of any material suitable for use in surgical applications, such as plastic. In one embodiment, body 10 is tapered at a first end 11. This helps to facilitate the placement of the device in the body of a surgical patient. Depending on the particular surgical application for which the device is to be used, body 10 may be shaped in a variety of ways in order to maximize the ability to position the device during the particular surgical procedure. For instance, body 10 may be generally straight and elongated, as shown in FIG. 1. Alternatively, if the device is to be used in a surgical application where it would be advantageous for the body to have a curved shape such that the body can more easily be positioned at a desired location in the patient, then body 10 may have a curved shape.

Additionally, if the device will be used to place sutures within the walls of a tissue cavity possessing a particular diameter, body 10 of the device may be designed to have a diameter commensurate with the size of the cavity to be sutured. This will facilitate the ability to position one or more needles within the cavity. Those skilled in the art will realize that the body may be shaped in a variety of ways to maximize the performance of the device in a given surgical application.

Figure 2A:
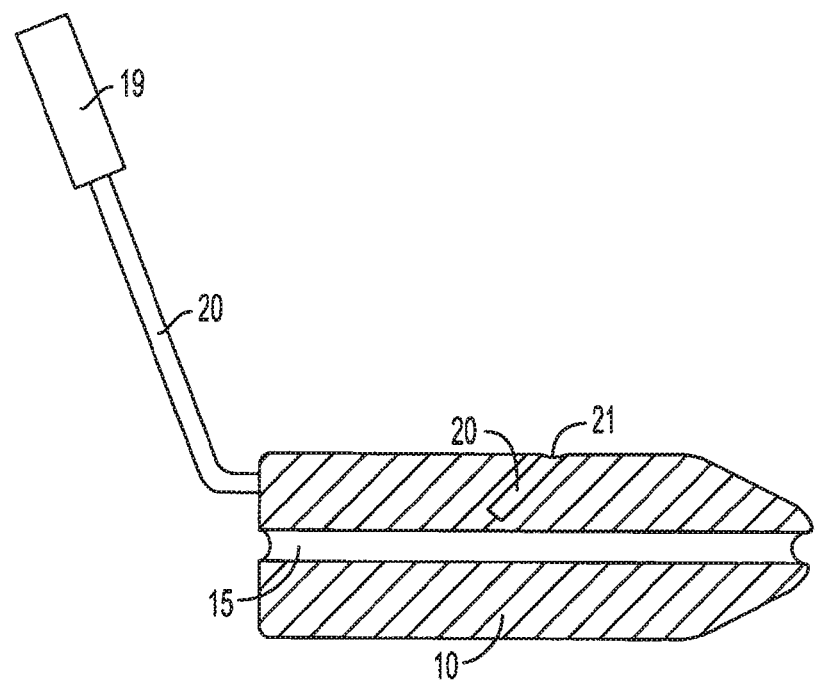
FIGS. 2A and 2B show various configurations of the needle guide channel in cross section.
Figure 2B:
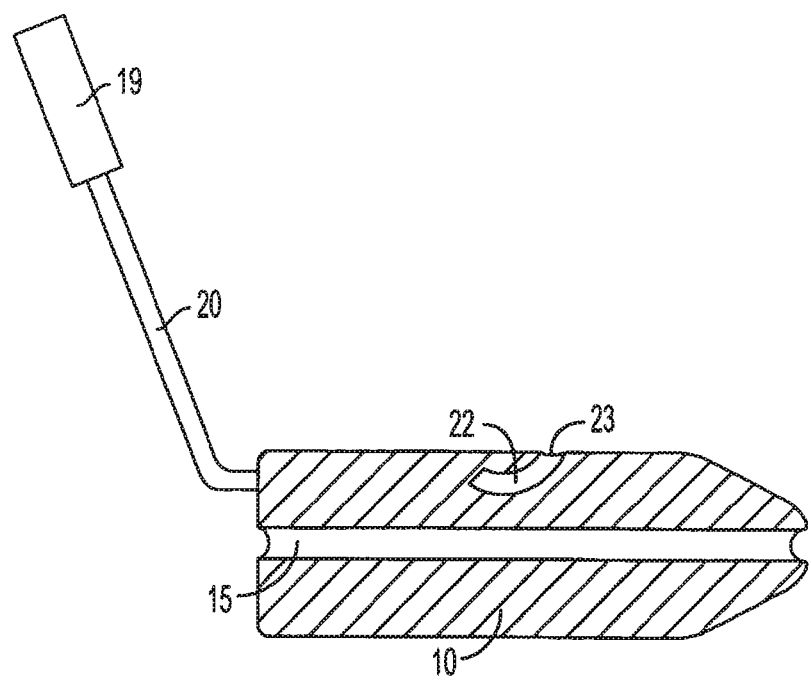

Body 10 also comprises one or more needle guide channels 12 that are formed in the body. The needle guide channel is configured to at least partially receive a needle that may be placed in the needle guide channel. As shown in FIG. 1, needle guide channel 12 extends from a first needle guide channel opening 13 formed in body 10 to a second needle guide channel opening 14 formed in the body 10. As shown in FIG. 1, needle guide channel 12 may be arcuate shaped, and may therefore be configured to receive an arcuate shaped needle. Those skilled in the art will realize that the needle guide channel may be configured in a variety of ways. For instance, needle guide channel 20 may extend from only a first needle guide channel opening 21 and be generally straight as shown in FIG. 2A. In another embodiment, needle guide channel 22 may be arcuate shaped, but extend from only a first needle guide channel opening 23, as shown in FIG. 2B. The needle guide channels may also be positioned at various positions along the body of the device. For example, the needle guide channels may be positioned nearer to first end 11 of body 10, nearer to second end 18 of body 10, or in approximately the middle of body 10. The positioning of the needle guide channels in the body of the device may be dictated by the area of the patient's body that is to be sutured. Those skilled in the art will realize that the needle guide channels may be positioned to maximize performance for suturing a particular area of a patient's body.

Figure 3A:
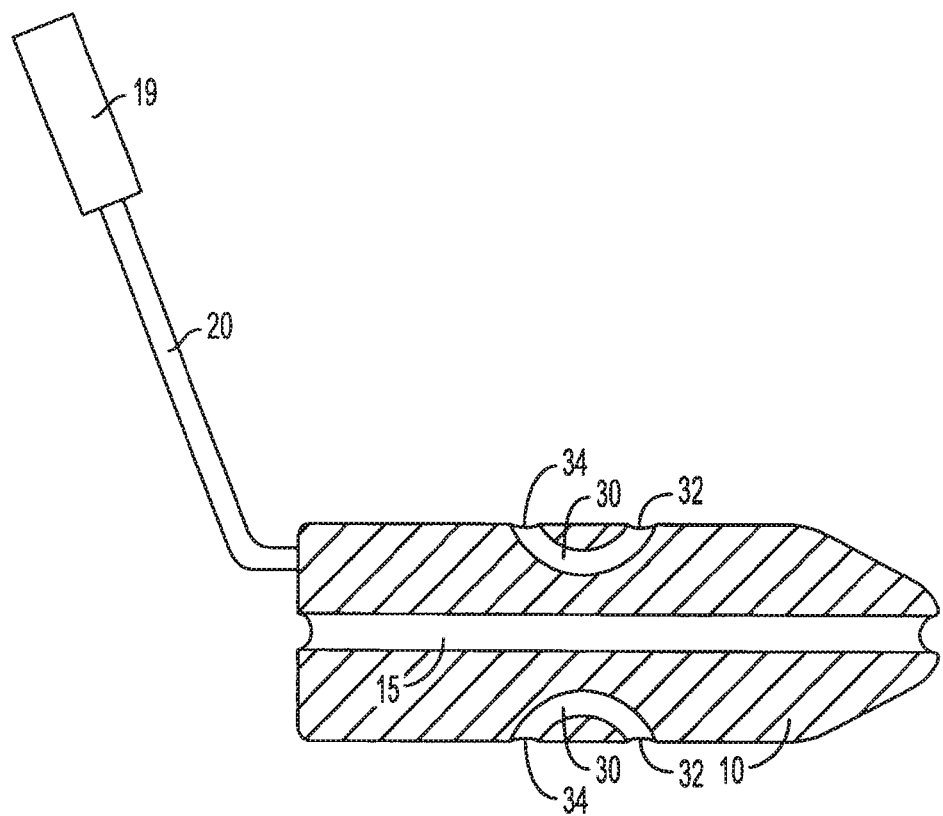
FIG. 3A shows an embodiment of the present invention in cross section that comprises multiple needle guide channels.
Figure 3B:
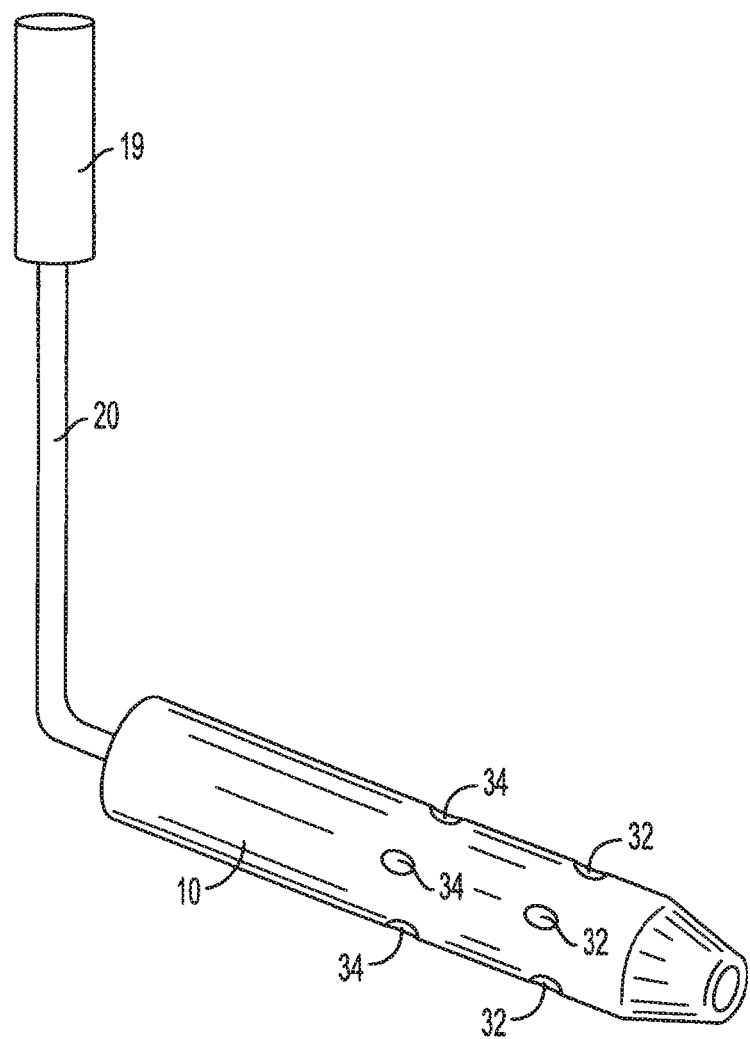
FIG. 3B shows a perspective view of one embodiment of the present invention having 6 needle guide channels (3 of which are not visible due to the orientation of the device).

Furthermore, the device may contain a plurality of needle guide channels. For example, the device of the present invention may have one, two, three, four, five, six, or more needle guide channels. The number of needle guide channels should fit the application. One embodiment of a device comprising multiple needle guide channels 30 is shown in FIG. 3A. As previously stated, the needle guide channels may have a variety of configurations, and each of the plurality of needle guide channels need not have the same configuration. In one embodiment, the needle guide channels are circumferentially positioned about the body of the device. In another embodiment, the needle guide channels are circumferentially positioned about the body of the device, and are approximately equidistantly spaced in relation to each other. A perspective view of such a device that has 6 needle guide channels 30 shown by their own first and second needle guide channel openings 32 and 34 appears in FIG. 3B (three of the sets of openings are not visible due to the orientation of the device). Such a configuration allows multiple needles to be uniformly positioned in a surgical patient when the needles are advanced out of the needle guide channels.

Figure 4A:
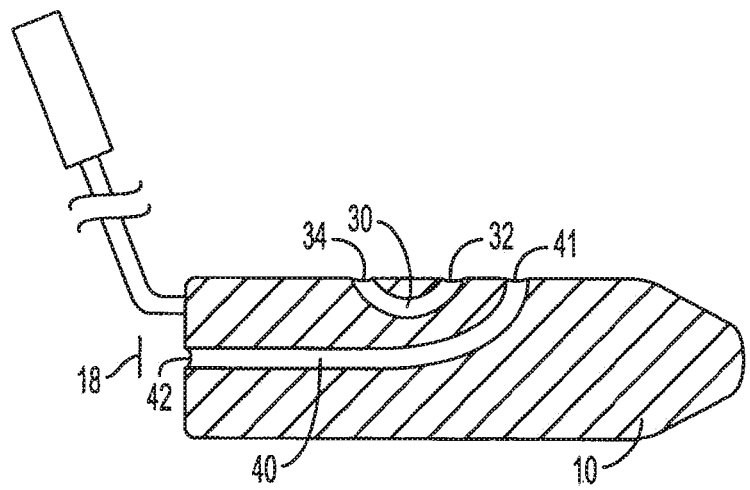
FIGS. 4A, 4B, and 4C are cross-sectional views depicting various configurations of the lumen.
Figure 4B:
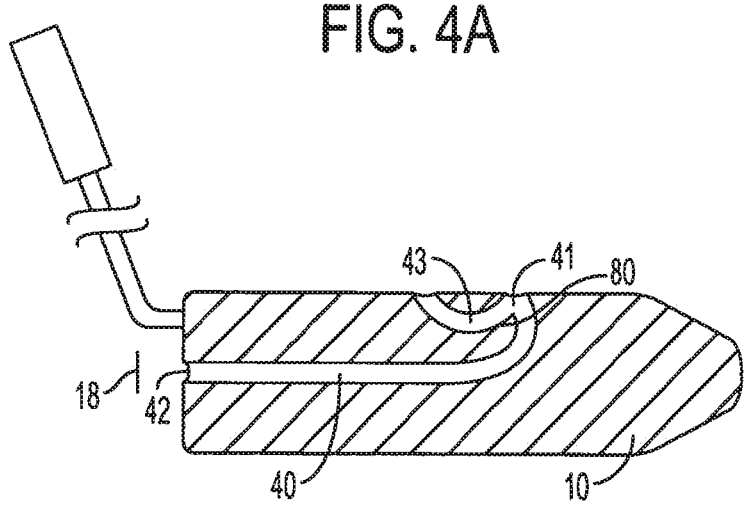

As shown in FIG. 1, the device of the present invention also comprises a lumen 15 that extends through body 10 from a first lumen opening 16 to a second lumen opening 17. The lumen should be of sufficient diameter that one or more sutures can be threaded through the lumen 15. The lumen may be configured in a variety of ways. For example, in the embodiment shown in FIG. 1, the lumen extends from first lumen opening 16 formed in first end 11 of body 10 to second lumen opening 17 formed in second end 18 of the body. Alternatively, as shown in FIG. 4A, lumen 40 may extend from first lumen opening 41 formed in the side of body 10 to second lumen opening 42 formed in second end 18 of body 10. In another embodiment shown in FIG. 4B, first lumen opening 41 may be formed in wall 80 of needle guide channel 43. In any embodiment, one of the lumen openings can be located at a position in the body of the device such that a person using the device will be easily able to grasp a suture that is extending from that lumen opening.

Figure 4C:
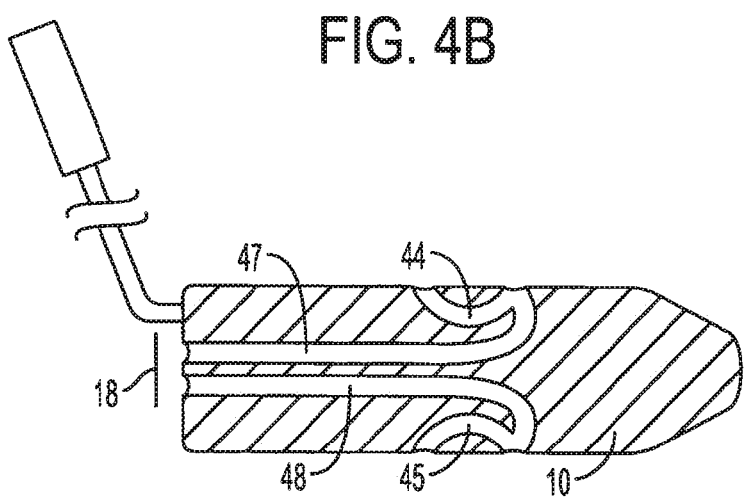

In another embodiment, more than one lumen may be formed in the body of the device. For example, each needle guide channel may have its own designated lumen. FIG. 4C shows one embodiment of the device in which first needle guide channel 44 and second needle guide channel 45 are formed in body 10. First lumen 47 and second lumen 48 are also formed in the body. First lumen 47 is positioned such that a suture coupled to a needle that is positioned in first needle guide channel 44 may be threaded through first lumen 47. Second lumen 48 is positioned such that a suture coupled to a needle that is positioned in second needle guide channel 45 may be threaded through second lumen 48. Those skilled in the art will recognize that the lumen or lumens of the present devices may be configured in a variety of other ways in addition to those described here.

As shown in FIG. 1, the device may also include a handle 19 that is connected to the body 10 by a connector piece, such as shaft 20. The handle may be made of any suitable material, such as plastic. The handle may be configured such that it can easily be grasped by one hand of a person using the device, such as by placing ergonomic indentions in the handle. In one embodiment, shaft 20 that connects handle 19 to body 10 may be bent in one or more places, as is shown in FIG. 1, in order to allow for the more accurate placement of the device during suturing. Those skilled in the art will realize that the connector piece may also be configured in a variety of other positions such that the configuration of the connector piece allows the body of the device to be maneuvered in a way that is most advantageous for the particular area being sutured. The connector piece may be made of a flexible material that allows the operator of the device to configure the connector piece in a variety of positions. The connector piece may be comprised of a number of suitable materials. One preferred material is stainless steel gauge wire. Furthermore, shaft 20 and handle 19 may be made from the same material so as to form a unitary structure, or different materials, as shown in the present figures.

Figure 5:
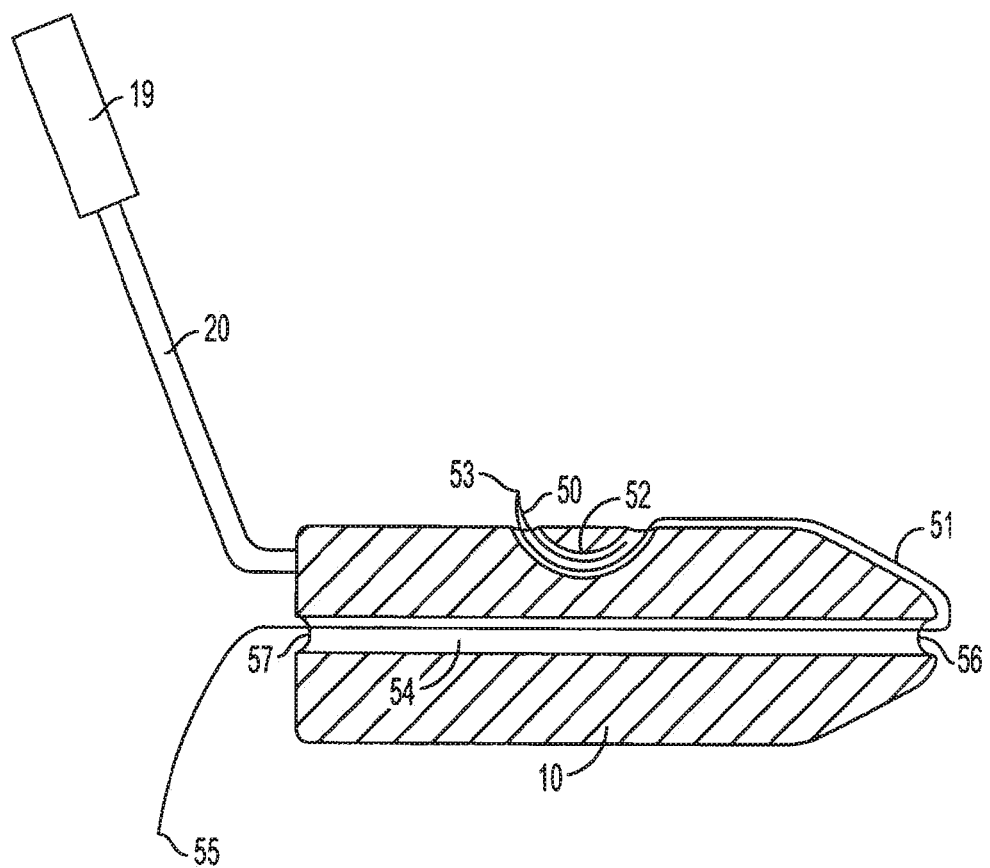
FIG. 5 shows one embodiment of the present invention in cross section, wherein a needle has been backloaded into the needle guide channel. A suture that is coupled to the needle has been threaded through the lumen.

An example of one embodiment of the present devices in which a needle 50 and suture 51 have been loaded is illustrated in FIG. 5. Suture 51 may be made from any material suited to the application, including an absorbable or chromic material used in urethral anastomosis cases. As shown in FIG. 5, needle 50 has been backloaded into needle guide channel 52. The term "backloaded" means that the needle is positioned in the needle guide channel such that it will be advanced, sharp end first, out of the needle guide channel by the suture when an end of the suture is pulled. First end 53 of the suture may be coupled to needle 50. As illustrated in FIG. 5, in one embodiment, suture 51 extends through needle guide channel 52, through first lumen opening 56, and through lumen 54 such that second end 55 of suture 51 extends out of second lumen opening 57. When the device is being used, the needle or needles will be positioned in their respective needle guide channels such that the sharp end or ends of the needle or needles are located within the needle guide channel or channels. This will prevent the needle or needles from becoming accidentally lodged in any tissue as the device is being positioned within the patient's body. Once the device has been positioned such that the needle guide channel opening nearest to the sharp end of the needle contained in the needle guide channel is adjacent to the location where it is desired that the needle be placed, the second end of the suture may be pulled to advance the needle into the desired location.

When the second end 55 of the suture is pulled outward from the second lumen opening, needle 50 is advanced out of needle guide channel 52. Because the needle is backloaded in the needle guide channel, the sharp end of the needle will be the leading end of the needle as the needle advances from the needle guide channel. When the second end of the suture is pulled outward from the second lumen opening, the needle advances out of the needle guide channel such that at least one of the directional components of the needle is opposite to at least one of the directional components of the second end of the suture. Thus, it is the suture itself that advances the needle out of the needle guide channel. Advantageously, this eliminates the need for the surgeon to manually grasp and position the needle in the tissue of the patient.

Figure 6:
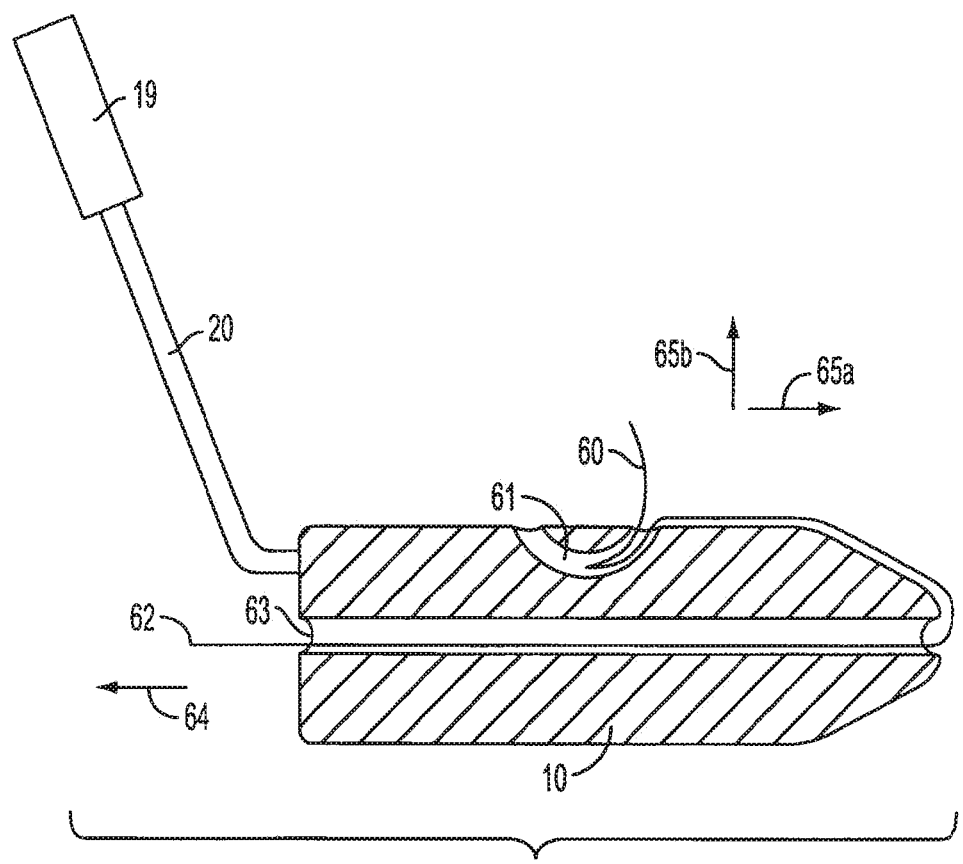
FIG. 6 shows one embodiment of the present invention in cross section, wherein a needle has been partially advanced out of the needle guide channel by pulling one end of the suture outward from one of the lumen openings.

FIG. 6 shows a needle 60 that has partly been advanced out of needle guide channel 61 by pulling the second end of suture 62 outward from the second lumen opening 63. One arrow 64 represents the direction in which the second end of the suture is pulled. Two arrows 65a and 65b represent the directional components of the needle as it is advanced out of the needle guide channel. As FIG. 6 shows, the needle has at least one directional component, represented by arrow 65a, that is opposite in direction to one of the directional components, represented by arrow 64, of the second end of the suture.

Figure 7A:
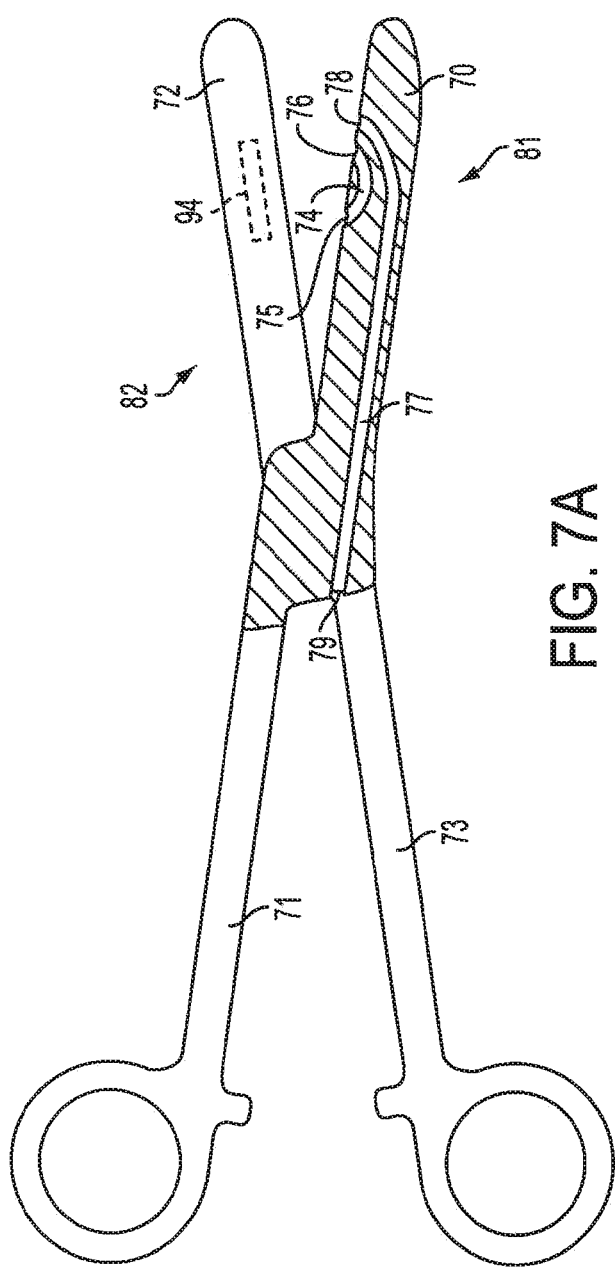
FIG. 7A shows one embodiment of the present invention in which a needle guide channel and a lumen have been formed in a first jaw of a clasping device.

FIG. 7A shows another embodiment of the present invention that takes the form of a clasping device, sometimes referred to as a hemostat. The clasping device shown in FIG. 7A includes a first member 81 (shown in partial cross section) having a first jaw 70 and a first handle 71, and a second member 82 having a second jaw 72 and a second handle 73. First and second members 81 and 82 may be pivotally connected to each other in any suitable fashion, including through the use of, for example, a pin or rivet. The respective jaws and handles of a given member may be portions of a single structure, or may be separate pieces of material coupled to each other in any suitable fashion, such as through interlocking parts, glue, welding, nuts and bolts, etc. The embodiment shown in FIG. 7A is particularly advantageous because the two jaws may be used to grip the area to be sutured, and then the needle can be placed at the desired location. A needle guide channel 74 is formed in first jaw 70.

Figure 7B:
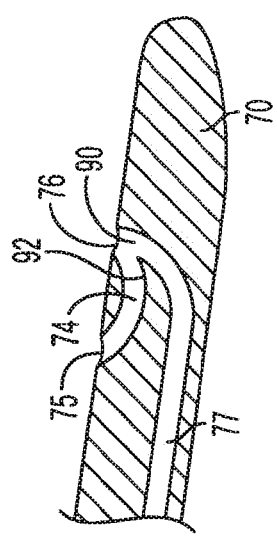
FIG. 7B is a view of a portion of a jaw of a clasping device according to one embodiment of the present invention, in which a needle guide channel and lumen have been formed in the same manner shown in FIG. 4B.

As was true of the previous embodiments, the needle guide channel may be configured in a variety of ways. For instance, needle guide channel 74 may extend from a first needle guide channel opening 75 to a second needle guide channel opening 76, as shown in FIG. 7A. Alternatively, the needle guide channel may only have one needle guide channel opening. The needle guide channel may also be shaped in various ways such that the needle guide channel is shaped to receive a needle of a specified shape. For instance, the needle guide channel may be arcuate shaped so as to receive an arcuate shaped needle (as shown in FIG. 7A), or may generally straight (as shown in FIG. 2A) so as to receive a traditional straight needle. In another embodiment, needle guide channel 74 may be arcuate shaped, but extend only from a first needle guide channel opening, such as needle guide channel 22 shown in FIG. 2B. In another embodiment, lumen 77 may extend from first lumen opening 90 formed in wall 92 of needle guide channel 74, as shown in FIG. 7B. In addition, the embodiment of the present invention shown in FIG. 7A may have multiple needle guide channels to facilitate the placement of multiple sutures, as discussed above with respect to body 10. Specifically, either or both jaws may have one or more needle guide channels, depending upon the application for which the clasping device will be used.

Figure 7C:
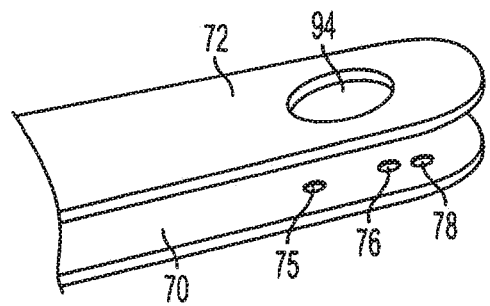
FIG. 7C shows a portion of the jaws of the clasping device in FIG. 7A from a perspective that reveals an opening in one of the two jaws through which a needle may be advanced.

As shown in FIG. 7A, second member 82 may have opening 94 (shown in dotted lines) disposed within second jaw 72. Opening 94 allows for a needle that is advanced out of needle guide channel 74 to advance without being obstructed by second jaw 72. FIG. 7C shows a perspective view of first and second jaws 70 and 72 and, in particular, opening 94. Opening 94 may be configured with any shape suited to allowing a needle advancing out of a relevant needle guide channel in one jaw to advance without obstruction from the other jaw. Multiple openings may be used as necessary when multiple needle guide channels are used.

As shown in FIG. 7A, in one embodiment, a lumen 77 that extends from a first lumen opening 78 to a second lumen opening 79 may also be formed in first jaw 70. The lumen should be of such a diameter that it may receive at least one suture that is threaded though the lumen. In another embodiment, a needle guide channel and lumen are also formed in the second jaw. As with the embodiments discussed above, in instances of multiple needle guide channels, one or more lumens may be used, such as the configuration discussed above in which each needle guide channel has its own lumen.

Figure 7D:
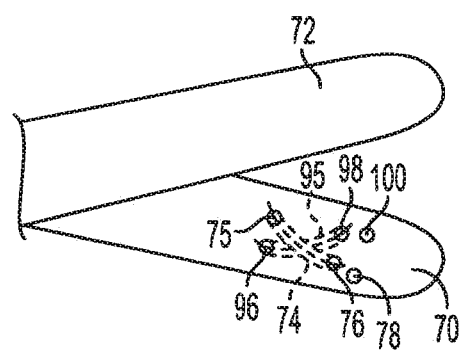
FIG. 7D shows a portion of the jaws of a clasping device according to another embodiment of the present invention, where one of the jaws includes two, crossed needle guide channels.

FIG. 7D shows the clasping device of FIG. 7A in which multiple needle guide channels are used. Specifically, in one embodiment, as shown in FIG. 7D, first jaw 70 may have two needle guide channels 74 and 95 (shown in dotted lines and which can be referred to as first and second needle guide channels). Needle guide channel 95, which extends from its respective first needle guide channel opening 96 to its respective second needle guide 100. A lumen—which is adapted to receive a length of suture and configured in operative relation with needle guide channel 95 such that when a length of suture is threaded through the lumen and is connected to a needle that is backloaded into needle guide channel 95, and the length of suture is pulled in a first direction, the needle is advanced out of needle guide channel 95 in a second direction—extends between a first lumen opening 100 to a second lumen opening (not shown). As shown in FIG. 7D, needle guide channels 74 and 95 cross each other.

The methods and devices of the present invention have a variety of uses. For example, the present devices may be used to place one or more needles for anastamosis of tubular-to-tubular structures, of tubular structure-to-skin as in colostomy or ileal loop diversion, or for suturing of tissue in a side-to-side fashion. As previously indicated, those skilled in the art will recognize that the design of the present devices may be easily adjusted to suit the location and position of the tissues to be sutured. Once a device has been used to place the needles in the desired location in the body of the surgical patient, the doctor may then grasp the needles, withdraw the device from the patient's body, and proceed with the suturing procedure.

One surgical specialty in which the present devices would be particularly useful is the radical prostatectomy. A radical prostatectomy requires the joining of the urethra to the bladder. This procedure is known as an anastamosis. The position of the urethra and the pubic bone are such that there is little flexibility in exposure for needle placement. The present invention is particularly well suited for suturing following a radical prostatectomy. For instance, one embodiment of the present invention may be used wherein multiple needles may be backloaded into needle guide channels that are located circumferentially around the body of the device. Each needle should have a suture coupled to it, and the sutures should be threaded through the lumen. The device may then be positioned within the urethra such that when the needles are advanced out of the needle guide channels, the needles will pierce the urethra, and will be positioned around the circumference of the urethra. After the needles have been advanced out of the needle guide channels, the doctor may then grasp the needles, withdraw the device from the body, and finish the suturing procedure.

Figure 8:
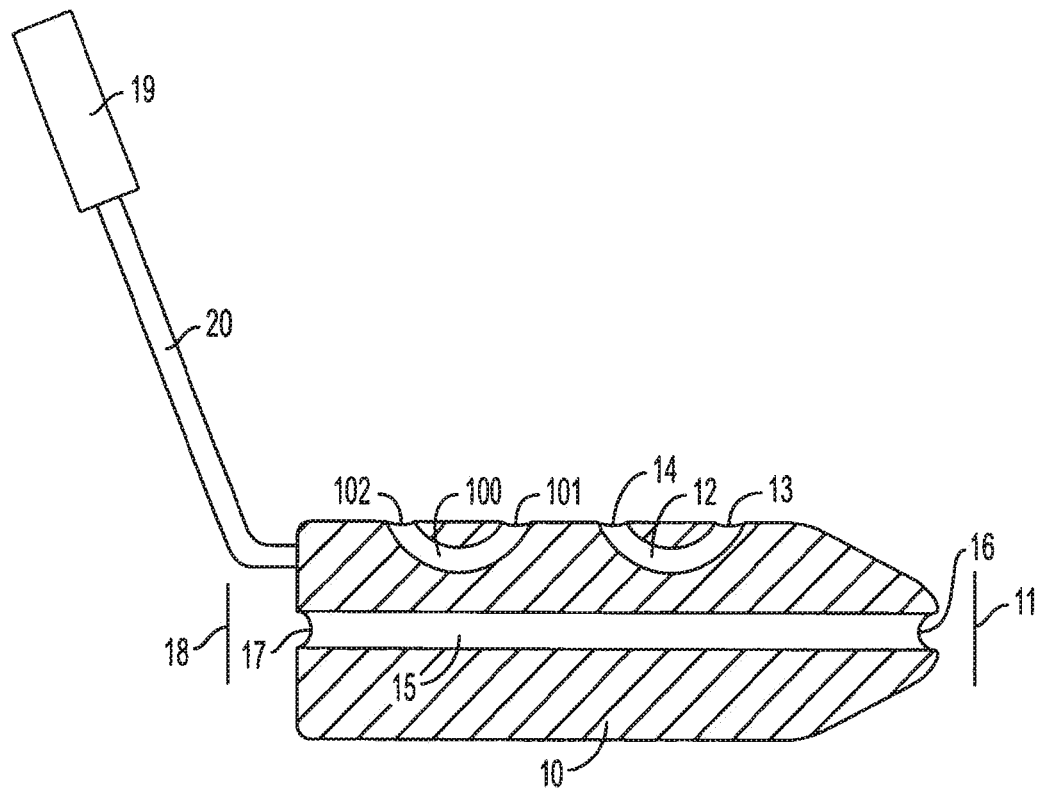
FIG. 8 shows an embodiment of the present invention in which two needle guide channels are staggered.

All of the medical devices and methods disclosed and claimed can be made and executed without undue experimentation in light of the present disclosure. While the medical devices and methods of this invention have been described in terms of certain embodiments, it will be apparent to those of skill in the art that variations may be applied to the medical devices and/or methods described herein without departing from the scope of the invention. For example, FIG. 8 shows an embodiment of the present medical devices in which two needle guide channels are staggered, unlike those shown in FIG. 3B. Specifically, FIG. 8, when compared to FIG. 1, shows the addition of needle guide channel 100, which extends from its own first needle guide channel opening 101 in body 10 to its own second needle guide channel opening 102 in body 10. As another example, multiple needle guide channels could be arranged circumferentially around the body of the present medical devices (or a jaw when the medical device is a clasping device) in two or more staggered groups, with one group being positioned at one distance from an end of the body (such as the distance between first needle guide channel opening 13 and first end 11 of body 10 in FIG. 8, for example), another group being positioned a second distance from the same end of the body (such as the distance between first needle guide channel opening 101 and first end 11 of body 10 in FIG. 8, for example), etc. Additionally, when multiple needle guide channels are positioned in a single medical device, the needle guide channels may have the same or different lengths. Further, the needle guide channels may cross each other, as shown in FIG. 7D. This is true even for needle guide channels disposed in the type of body depicted in FIG. 3B, for example.

I claim:

1. A medical device comprising:
   a first member having a proximal portion comprising a first handle and a distal portion comprising first jaw, the first jaw having:
      a first lumen extending from a first lumen opening formed in the first jaw to a second lumen opening formed in the first jaw, the first lumen adapted to receive a length of suture; and
      a first needle guide channel extending from a first needle guide channel opening formed in the first jaw;
   a second member having a proximal portion comprising a second handle and a distal portion comprising second jaw, the second member pivotally connected to the first member, the first and second jaws configured to grip an area to be sutured; and
   a curved needle backloaded into the first needle guide channel, wherein the backloading includes a proximal longitudinal component, the needle connected to a length of suture threaded through the first lumen;
   wherein the first lumen and first needle guide channel are configured in operative relation with each other such that the needle will be advanced out of the first needle guide channel by pulling in a direction having a proximal longitudinal component on the length of suture.

2. The medical device of claim 1, wherein the first needle guide channel is arcuate shaped.

3. The medical device of claim 1, further comprising:
   one or more additional needle guide channels, each extending from its own first needle guide channel opening formed in the first jaw;
   wherein each of the one or more additional needle guide channels is configured in operative relation with the lumen such that a needle that is backloaded into any of the one or more additional needle guide channels will be advanced out of the additional needle guide channel by pulling on a length of suture that is connected to the needle and threaded through the lumen.

4. The medical device of claim 3; wherein one of the one or more additional needle guide channels is arcuate shaped.

5. The medical device of claim 3, wherein each of the one or more additional needle guide channels and the first needle guide channel are arcuate shaped.

6. The medical device of claim 1, wherein the second jaw comprises:
   a second lumen extending from a third lumen opening formed in the second jaw to a fourth lumen opening formed in the second jaw, the second lumen adapted to receive a length of suture; and
   a second needle guide channel extending from a second needle guide channel opening formed in the second jaw;
   wherein the second lumen and second needle guide channel are configured in operative relation with each other such that a needle that is backloaded into the second needle guide channel will be advanced out of the second needle guide channel by pulling on a length of suture that is connected to the needle and threaded through the second lumen.

7. The medical device of claim 6, wherein the second needle guide channel is arcuate shaped.

8. The medical device of claim 7, wherein the first and second needle guide channels cross each other.

9. The medical device of claim 6, further comprising:
   one or more additional needle guide channels, each extending from its own second needle guide channel opening formed in the second jaw;
   wherein each one or more additional needle guide channel is configured in operative relation with the second lumen such that a needle that is backloaded into any of the one or more additional needle guide channels will be advanced out of the additional needle guide channel by pulling on a length of suture that is connected to the needle and threaded through the second lumen.

10. The medical device of claim 9, wherein one of the one or more additional needle guide channels is arcuate shaped.

11. The medical device of claim 9, wherein each of the one or more additional needle guide channels and the first needle guide channel are arcuate shaped.

12. The medical device of claim 1, wherein the first member comprises multiple pieces.

13. A medical device comprising:
   a first member having a proximal portion comprising a first handle and a distal portion comprising first jaw, the first jaw having a first lumen extending from a first lumen opening to a second lumen opening, the first lumen adapted to receive a length of suture, the first jaw also having a first needle guide channel that is arcuate shaped; and
   a second member having a proximal portion comprising a second handle and a distal portion comprising second jaw, the second member pivotally connected to the first member, the first and second jaws configured to grip an area to be sutured;
   wherein the first lumen and first needle guide channel are configured in operative relation with each other such that a needle that is backloaded into the first needle guide channel wherein the backloading includes a proximal longitudinal component, will be advanced by pulling in a direction having a proximal longitudinal component on a length of suture that is connected to the needle and threaded through the first lumen.

14. The medical device of claim 13, wherein the first member comprises multiple pieces.

* * * * *